US009193992B2

(12) United States Patent
Curry et al.

(10) Patent No.: US 9,193,992 B2
(45) Date of Patent: Nov. 24, 2015

(54) METHOD FOR DETERMINING PLOIDY OF A CELL

(71) Applicant: Agilent Technologies, Inc., Loveland, CO (US)

(72) Inventors: Bo U. Curry, Redwood City, CA (US); Jayati Ghosh, Cupertino, CA (US); Brian Jon Peter, Los Altos, CA (US); Arjun Vadapalli, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 190 days.

(21) Appl. No.: 13/894,886

(22) Filed: May 15, 2013

(65) Prior Publication Data

US 2013/0323730 A1    Dec. 5, 2013

Related U.S. Application Data

(60) Provisional application No. 61/655,914, filed on Jun. 5, 2012.

(51) Int. Cl.
*C12Q 1/68* (2006.01)
*C07H 21/00* (2006.01)
*G06F 19/18* (2011.01)

(52) U.S. Cl.
CPC ............ *C12Q 1/6827* (2013.01); *C12Q 1/6883* (2013.01); *G06F 19/18* (2013.01); *C12Q 2600/158* (2013.01)

(58) Field of Classification Search
CPC ........ C12Q 1/68; C12Q 1/6827; C07H 21/00; C07H 21/02; C07H 21/04
See application file for complete search history.

(56) References Cited

U.S. PATENT DOCUMENTS

| | | | |
|---|---|---|---|
| 2003/0082566 A1* | 5/2003 | Sylvan ............... | 435/6 |
| 2004/0157243 A1* | 8/2004 | Huang et al. ............ | 435/6 |
| 2006/0078891 A1* | 4/2006 | Ach et al. ............ | 435/6 |
| 2006/0080043 A1* | 4/2006 | Sampas et al. ............ | 702/20 |
| 2006/0110744 A1* | 5/2006 | Sampas et al. ............ | 435/6 |
| 2006/0252071 A1* | 11/2006 | Lo et al. ............ | 435/6 |
| 2008/0070792 A1* | 3/2008 | Stoughton et al. ............ | 506/9 |
| 2008/0138809 A1* | 6/2008 | Kapur et al. ............ | 435/6 |
| 2008/0220422 A1* | 9/2008 | Shoemaker et al. ............ | 435/6 |
| 2009/0291443 A1* | 11/2009 | Stoughton et al. ............ | 435/6 |
| 2010/0215645 A1* | 8/2010 | Cargill et al. ............ | 424/130.1 |
| 2011/0288780 A1* | 11/2011 | Rabinowitz et al. ............ | 702/19 |
| 2011/0301854 A1* | 12/2011 | Curry et al. ............ | 702/19 |
| 2012/0270212 A1* | 10/2012 | Rabinowitz et al. ......... | 435/6.11 |
| 2013/0013631 A1* | 1/2013 | Rodinger et al. ............ | 707/769 |
| 2013/0261984 A1* | 10/2013 | Eberle et al. ............ | 702/20 |

OTHER PUBLICATIONS

Adinolfi et al.,Rapid Detection of Aneuploidies by Microsatellite and the Quantitative Fluorescent Polymerase Chain Reaction. Prenatal Diagnosis 17 (13) : 1299 (1997).*
Attiyeh et al., Genomic copy number determination in cancer cells from single nucleotide polymorphism microarrays based on quantitative genotyping corrected for aneuploidy. Genome Research 19 : 276 (2009).*
Bianchi, D.W., Will Epigenetic Allelic Ratio Analysis Turn Prenatal Diagnosis of Trisomy 18 on Its EAR? Clinical Chemistry 52(12) :2182 (2006).*
Carvalho et al. Exploration, normalization, and genotype calls of high-density oligonucleotide SNP array data. Biosrtatistics 8 (2) : 485 (2007).*
Chiu et al. Noninvasive prenatal diagnosis of fetal chromosomal aneuploidy by massively parallel genomic sequencing of DNA in maternal plasma. PNAS 105 (51) : 20458 (2008).*
Corver et al. Genome-wide Allelic State Analysis on Flow-Sorted Tumor Fractions Provides an Accurate Measure of Chromosomal Aberrations. Cancer Research 68 (24) : 10333 (2008).*
Dudarewicz et al. Molecular Methods for rapid detection of aneuploidy. Review Article Journal of Applied Genetics 46 (2) : 207 (2005).*
Dudoit et al.Statistical Methods for Identifying Differentially Expressed Genes in Replicated cDNA Microarray Experiments. Statistica Sinica 12 : 111 (2002).*
Gardina et al., Ploidy status and copy number aberrations in primary glioblastomas defined by integrated analysis of allelic ratios, signal ratios and loss of heterozygosity using 500K SNP Mapping Arrays. BMC Genomics 9 : 489 (2008).*
Gutierrez-Mateo et al. Validation of microarray comparative genomic hybridization for comprehensive chromosome analysis of embryos. Fertility and Sterility 95(3) : 953 (Mar. 2011).*
Herr et al.High-resolution analysis of chromosomal imbalances using the Affymetrix 10K SNP genotyping chip. Genomics 85 :392 (2005).*
Irizarry et al. Exploration, normalization, and summaries of high density oligonucleotide array probe level data. Biostatistics 4 (2) : 249 (2003).*
Levett et al. A large-scale evaluation of amnio-PCR for the rapid prenatal diagnosis of fetal trisomy. Ultrasound in Obstetrics and Gynecology 17 : 115 (2001).*
Li et al., SNP detection for massively parallel whole-genome resequencing. Genome Research 19 : 1124 (2009).*
Lo et al., Prenatal diagnosis: progress through plasma nucleic acids. Nature Reviews Genetics 8 : 71 (2007).*
Lo et al., Plasma placental RNA allelic ratio permits noninvasive prenatal chromosomal aneuploidy detection. Nature Medicine 13(2) : 218 (2007).*
Lo et al. Digital PCR for the molecular detection of fetal chromosomal aneuploidy. PNAS 104 (32) : 13116 (2007).*
Lo et al.,Noninvasive Prenatal Diagnosis of Fetal Chromosomal Aneuploidies by Maternal Plasma Nucleic Acid Analysis. Clinical Chemistry 54 (3) : 461 (2008).*

(Continued)

*Primary Examiner* — Ethan C Whisenant

(57) ABSTRACT

A method for determining the ploidy of a test genome is provided. In some embodiments, the method may comprises: a) obtaining a plurality of ratios for polymorphisms that are distributed throughout a test genome, wherein each of the ratios is a ratio of the measured copy number of uncut allele in a polymorphic site relative to the measured copy number of the uncut allele in the reference sample; b) taking the log of the ratios and plotting a distribution of the reference corrected log ratios of the SNP probes; and c) determining the ploidy of said the genome based on the number of peaks in that distribution.

20 Claims, 6 Drawing Sheets

(56) References Cited

OTHER PUBLICATIONS

Oosting et al., High-resolution copy number analysis of paraffin-embedded archival tissue using SNP BeadArrays. Genome Research 17 : 368 (2007).*

Paulson et al., Loss of Heterozygosity Analysis Using Whole Genome Amplification, Cell Sorting, and Fluorescence-Based PCR. Genome Research 9 : 482 (1999).*

Point-Kingdon et al. Rapid Detection of Aneuploidy (Trisomy 21) by Allele Quantification Combined with Melting Curves Analysis of Single-Nucleotide Polymorphism Loci. Clinical Chemistry 49(7) : 1087 (2003).*

Quakenbush, J. Microarray data normalization and transformation. Nature Geneic(supplement) 32 : 496 (2002).*

Raychaudhuri et al., Basic microarray analysis: grouping and feature reduction. Trends in Biotechnology 19(5) :189 (2001).*

Simon-Sanchez et al., Genome-wide SNP assay reveals structural genomic variation, extended homozygosity and cell-line induced alterations in normal individuals. Human Molercular Genetics 16(1) : 1-14 (2006).*

Shen et al., A SNP discovery method to assess variant allele probability from next-generation resequencing data. Genome Research 20 : 273 (2010).*

Slater et al., High-Resolution Identification of Chromosomal Abnormalities Using Oligonucleotide Arrays Containing 116,204 SNPs. American J. Of Human Genetics 77 : 709 (2005).*

SNP Working Group, A map of human genome sequence variation containing 1.42 million single nucleotide polymorphisms. Nature 409 : 928 (2001).*

Su et al.*

Tong et al. Noninvasive Prenatal Detection of Fetal Trisomy 18 by Epigenetic Allelic Ratio Analysis in Maternal Plasma: Theoretical and Empirical Considerations. Clinical Chemistry 52 (12) :2194 (2006) + Supplemental data.*

Treff et al. SNP microarray-based 24 chromosome aneuploidy screening is significantly more consistent than FISH. Molecular Human Reproduction 16 (8) : 583 (2010).*

Treff et al., Accurate single cell 24 chromosome aneuploidy screening using whole genome amplification and single nucleotide polymorphism microarrays. Fertility and Sterility 94 (6) : 2017 (2010).*

Trewick et al., Accurate Single-Nucleotide Polymorphism Allele Assignment in Trisomic or Duplicated Regions by Using a Single Base-Extension Assay with MALDI-TOF Mass Spectrometry. Clinical Chemistry 57 (8) : 1188 (2011).*

Verma et al., Rapid and simple prenatal DNA diagnosis of Down's syndrome. The Lancet 352 :9 (1998).*

Zhao et al., An Integrated View of Copy Number And Allelic Alterations in the Cancer Genome Using Single Nucleotide Polymorphism Arrays. 64 : 3060 (2004).*

ARUP Laboratories., Genomic SNP Microarray, Products of Conception (ARRAY POC)., www.aruplab.com, 2012, pp. 1-3.

Lathi, et al., Informatics Enhanced SNP Microarray Analysis of 30 Miscarriage Samples Compared to Routine Cytogenetics., PLoS ONE, 2012, 7:e31282, pp. 1-5.

Reddy, et al., The role of DNA microarrays in the evaluation of fetal death. Prenatal Diagnosis. 2012, 32:371-75.

Srebniak, et al., Genomic SNP array as a gold standard for prenatal diagnosis of foetal ultrasound abnormalities. Molecular Cytogenetics, 2012, 5:14, pp. 1755-8166.

* cited by examiner

METHOD FOR DETERMINING PLOIDY OF A CELL

CROSS REFERENCING

This application claims the benefit of U.S. Provisional Application Ser. No. 61/655,914, filed Jun. 5, 2012, which application is incorporated by reference herein.

INTRODUCTION

Normal humans have two sets of 23 chromosomes in every diploid cell, with one set from each parent. Cells that contain an additional haploid set of chromosomes are known as triploid. Triploidy is thought to the cause of up to 20% of spontaneous abortions, premature births and perinatal death. The genome of a triploid cell may be characterized as being 69, XXX or 69, XXY or 69, XYY, depending on how the triploidy occurred. Tetraploid cells have two additional haploid sets of chromosomes. This disclosure provides a way of determining the ploidy of a cell.

DEFINITIONS

Figure 1:
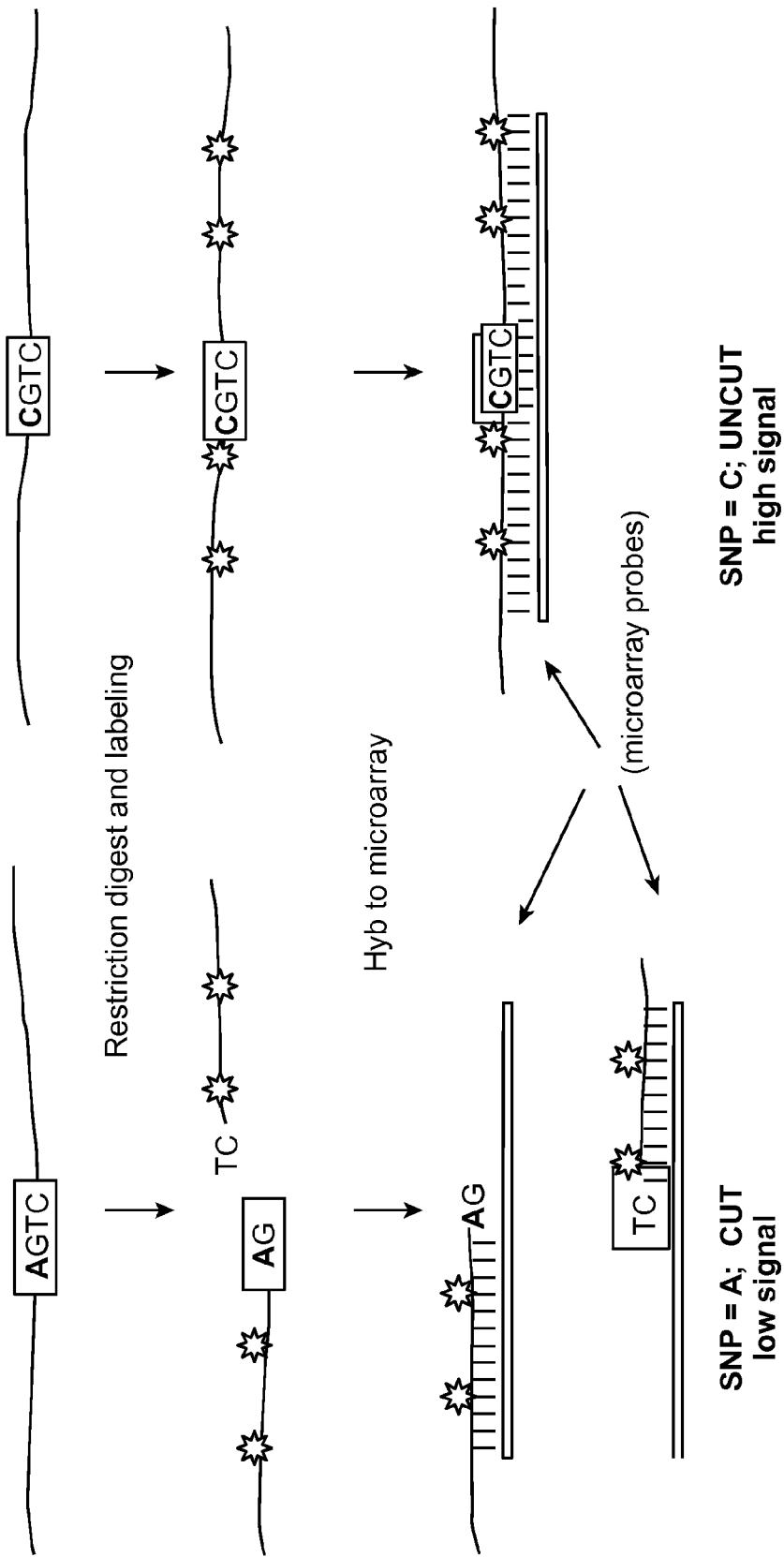
FIG. 1 illustrates one exemplary method for identifying which alleles of a SNP are present in a sample.

The term "sample", as used herein, relates to a material or mixture of materials, typically, although not necessarily, in liquid form, containing one or more analytes of interest.

The term "genome", as used herein, refers to the nuclear DNA of an organism. The term "genomic DNA" as used herein refers to deoxyribonucleic acids that are obtained from the nucleus of an organism. The terms "genome" and "genomic DNA" encompass genetic material that may have undergone amplification, purification, or fragmentation. In some cases, genomic DNA encompasses nucleic acids isolated from a single cell, or a small number of cells. The "genome" in the sample that is of interest in a study may encompass the entirety of the genetic material from an organism, or it may encompass only a selected fraction thereof: for example, a genome may encompass one chromosome from an organism with a plurality of chromosomes. The terms "genome" and "genomic DNA" do not encompass cDNA (which is cDNA made from RNA). However, as is well known, information about a cell's genome (e.g., about SNPs etc) can be obtained from examining cDNA from that cell.

The term "genomic region" or "genomic segment", as used herein, denotes a contiguous length of nucleotides in a genome of an organism. A genomic region may be of a length as small as a few kb (e.g., at least 5 kb, at least 10 kb or at least 20 kb), up to an entire chromosome or more.

The terms "test", as used herein with reference to a type of sample (e.g., a genome), refers to a sample that is under study.

The term "reference," as used herein with reference to a type of sample, refers to a sample to which a test sample may be compared. A reference sample from the same species (e.g., where the species is human, or mouse, for example) as that of the test sample. The reference sample may represent an individual genome, e.g., of a cell line, or may represent either a physical pooling of the genomes of multiple individuals or a computational combination of data from a number of individuals. A "reference sample" presumes that the genotype corresponding to the polymorphic sites of the reference sample is known. In some cases, the genotype of the reference sample is known from previously measured array results, or from sequencing. In other cases, the reference contains a region of known nucleotide sequence, e.g. a chromosomal region whose sequence is deposited at NCBI's Genbank database or other databases, for example. In one embodiment, a reference genome is of known genotype and is diploid everywhere, except on sex chromosomes.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, uracil and thymine (G, C, A, U and T, respectively).

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to the corresponding nucleotides in the target nucleic acid.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional and three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "hybridization conditions" as used herein refers to hybridization conditions that are optimized to anneal an oligonucleotide of a sufficient length to a probe, e.g. an oligonucleotide that is not nicked and has a contiguous length of at least 20 nucleotides (e.g. at least 30, at least 40, up to at least 50 or more) complementary to a nucleotide sequence of the probe. In certain cases, hybridization conditions may provide for dissociation of duplexes that anneal over a short length of region (e.g. less than 50, less than 40, less than 30, or less than 20 contiguous nucleotides) but not dissociation of duplexes formed between an un-nicked strand and its respective probe. Such conditions may differ from one experiment to the next depending on the length and the nucleotide content of the complementary region. In certain cases, the temperature for low-stringency hybridization is 5°-10° C. lower than the calculated $T_m$ of the resulting duplex under the conditions used. Details on the hybridization conditions suitable for use in certain embodiments in the present disclosure may be found in US Patent Publication 20090035762, the disclosure of which is incorporated herein by reference.

As used herein, the term "data" refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

As used herein, the term "plurality" refers to at least 2, e.g., at least 5, at least 10, at least 20, at least 50, at least 100, at least 500, at least 1,000, at least 5,000 or at least 10,000 or more, up to 50,000, or 100,000 or more.

As used herein, the term "homozygous" denotes a genetic condition in which identical alleles reside at the same loci on homologous chromosomes.

As used herein, the term, "heterozygous" denotes a genetic condition in which different alleles reside at the same loci on homologous chromosomes.

As used herein, the term "ploidy" refers to the number of haploid genomes contained in a cell. Diploid, triploid and tetraploid are kinds of ploidy.

As used herein, the term "diploid" refers to genomic regions that exist in a cell with a copy number of two, i.e., twice the haploid number. For example, a reference assembly of the human genome includes approximately $3 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of X chromosomes (female) for a total of 46 chromosomes. In a typical diploid cell, the autosomes are diploid.

As used herein, the term "aneuploid" refers to a cell having less than or more than the normal diploid number of chromosomes. Aneuploidy refers to any deviation from euploidy, including conditions in which only some regions of a single chromosome are missing or added.

The two most commonly observed forms of aneuploidy are monosomy and trisomy. Monosomy is lack of one of a pair of chromosomes. An individual having only one chromosome 6 is said to have monosomy 6. A common monosomy seen in many species is X chromosome monosomy, also known as Turner's syndrome. Monosomy is most commonly lethal during prenatal development. Trisomy is having three chromosomes of a particular type. A common autosomal trisomy in humans is Down syndrome, or trisomy 21, in which a person has three instead of the normal two chromosome 21s. Trisomy is a specific instance of polysomy, a more general term that indicates having more than two of any given chromosome.

Another type of aneuploidy is "triploidy". A triploid individual has, on average, three of every chromosome, that is, three haploid sets of chromosomes. A constitutively triploid human would have 69 chromosomes (3 haploid sets of 23). Production of triploids is relatively common and can occur by, for example, fertilization by two sperm. However, birth of a live human triploid is rare and such individuals are quite abnormal. The rare triploids that survive for more than a few hours after birth are thought to be mosaics, having a large proportion of diploid cells. Tumors, however, are not infrequently triploid.

The term "tetraploid" refers to a cell having two additional haploid sets of chromosomes.

As used herein, the term "single nucleotide polymorphism", or "SNP" for short, refers to a phenomenon in which two or more alternative alleles (i.e., different nucleotides) are present at a single nucleotide position in a genomic sequence at appreciable frequency (e.g., often 1%) in a population. In some cases, SNPs may be present at a frequency less than 1% in a population. As used herein, the term SNP may include these "rare SNPs" (present at a frequency less than 1% in a population) or even "single nucleotide variants" (SNVs) that have only been detected in one or a few samples to date.

As used herein, the term "SNP site" denotes the position of a SNP in a genomic sequence. A SNP site may be indicated by genomic coordinates. The nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's online dbSNP database, and the online database of the International HapMap Project; see also Teufel et al 2006 *Current bioinformatics tools in genomic biomedical research* Int. J. Mol. Med. 17:967-73).

As used herein, the term "SNP allele" refers to the identity of the nucleotide at a SNP site (e.g., whether the SNP site has a G, A, T or C). A "first allele" and a "second allele" of a SNP are different alleles, i.e., they have different nucleotides at the SNP site.

As used herein, the term "allele-specific copy number" indicates the number of copies of a particular SNP allele in a cell of a sample. For example, in many cases a SNP site of single chromosome can be occupied by either the first allele or the second allele of the SNP. In a diploid genome that SNP site can be: a) homozygous for the first allele of the SNP (in which case the allele-specific copy number of the first allele of the SNP is "2" and the allele-specific copy number of the second allele of the SNP is "0"), b) heterozygous (in which case the allele-specific copy number of the first allele of the SNP is "1" and the allele-specific copy number of the second allele of the SNP is also "1"), or c) homozygous for the second allele of the SNP (in which case the allele-specific copy number of the first allele of the SNP is "0" and the allele-specific copy number of the second allele of the SNP is "2"). In non-diploid regions, the copy number of a SNP allele may in be certain cases greater than 2. In case of a SNP that is present in a region with a copy number of four, the copy number of a SNP allele in that region can be 0, 1, 2, 3 or 4.

The term "loss of heterozygosity" or "LOH" for short, indicates that a region of a test genome has lost heterozygosity relative to a parent genome or to a diploid reference genome. Loss of heterozygosity may be caused by several biological mechanisms, including, but not limited to, deletion of one copy of a region of a diploid chromosome, or UniParental Disomy (UPD) which can occur by trisomy within a fertilized egg, followed by loss of one copy of the chromosome, known as "trisomy rescue". In cancer cells, LOH is frequently caused by a somatic chromosomal rearrangement.

The term "copy number neutral loss of heterozygosity" refers to a region of a test genome that lacks heterozygosity but whose copy number is the same as a diploid reference genome. Copy number neutral LOH can occur when both copies of a genomic region in a diploid genome are contributed by a single parent, by parental consanguinity, or by a gene conversion event in which a locus in a first chromosomes of homologous chromosomes is replaced by the same locus in the second chromosome of the pair, leaving two copies of the second locus. Copy number neutral loss of heterozygosity is also known as uniparental disomy or acquired uniparental disomy. Copy number neutral loss of heterozygosity is common in both hematologic and solid tumors, and is thought to constitute 20 to 80% of the loss of heterozygosity observed in human tumors. Copy-neutral LOH cannot be detected by traditional CGH, FISH, or cytogenetics methods. A region that has lost heterozygosity can be identified as such because all the SNPs in the region are homozygous (i.e., from one parent or the other) rather than heterozygous. Copy number neutral loss of heterozygosity is further described in Mao et al (Curr Genomics. 2007 8: 219-28), Gondek et al (Blood 2008 111: 1534-42); Beroukhim et al (PLoS Comput. Biol. 2006 2:e41); Ishikawa et al (Biochem. Biophys. Res. Commun.) 2005 333:1309-14) and Lo et al (Genes Chrom. Cancer. 2008 47: 221-37).

The term "data" refers to both raw data and processed data. Raw data may be processed, e.g., normalized, smoothed, filtered, etc., prior to use in the subject method using any suitable method (see, e.g., Quackenbush, Nat. Gen. 2002 Supp. 32, van Houte et al BMC Genomics. 2009; 10:401 and Staaf et al BMC Genomics. 2007 8:382, Staaf et al BMC Bioinformatics. 2008 9:409, Rigaill et al Bioinformatics. 2008 24:768-74, Curry et al Normalization of Array CGH Data In Methods in Microarray Pages 233-244 Normalization CRC Press 2008; incorporated by reference for all data processing steps, among many others).

The term "obtaining" refers to any way of coming into possession of something, including accessing a data file in silico, as well as receiving a data file from a remote location.

The term "SNP data" refers to data obtained from an assay in which the SNPs of a test sample are analyzed. In certain cases the test sample may be analyzed relative to a reference sample in order to determine which SNP alleles are present in the test sample. Such an assay may be done by a wide variety of methods, including those of US20090035762, Mei et al (Genome Res. 2000 10: 1126-37) or Gunderson et al (Nat Genet. 2005 37:549-54), for example. In further embodiments, the assay may be done by sequencing a sample. In one embodiment, the assays involve comparing the level of hybridization of a test sample to a SNP-discriminating oligonucleotide relative to the level of hybridization of a reference sample to the same oligonucleotide. The ratio of hybridization indicates the relative numbers of copies of one of the SNP alleles present in the sample and the reference. With respect to SNP data, the term "ratio" refers to a value that indicates the allele-specific copy number of a SNP. The term "ratio" includes functions or transformations of a ratio, such as a log of a ratio.

With reference to the SNP data, the term "log$_2$ ratio" indicates the log base two of the ratio of the measured allele specific copy number of a SNP.

The terms "CGH data" and "comparative genomic hybridization data" refers to data obtained from an assay in which the relative copy number of the same locus in two samples (e.g., a test sample and a reference sample) is determined. The general principles of a CGH assay are described in Barrett et al (Proc Natl Acad Sci 2004 101:17765-70) and Hostetter et al (Nucleic Acids Res. 2010 38: e9), for example. Such assays involve comparing the level of hybridization of a test sample to an oligonucleotide relative to the level of hybridization of a reference sample to the same oligonucleotide. The ratio of hybridization indicates the relative copy numbers of a sequence in the sample. Hybridization may be measured by several means, for example, fluorescent signal bound to a solid support such as a microarray. As another example, hybridization may be measured by the number of aligned sequence reads obtained from a test sample and reference sample after target enrichment.

With reference to the CGH data, the term "log$_2$ ratio" indicates the log base two of the ratio of the amount of hybridization of a test sample to an oligonucleotide relative to the amount of hybridization of the oligonucleotide to a reference sample.

The term "probability distribution function" is a continuous probability density function that identifies the probability of a value falling within a particular interval. A probability distribution clusters around a single mean value and describes the range of possible values that a random variable can attain and the probability that the value of the random variable is within any measurable subset of that range. Probability distribution functions include normal (i.e., Gaussian) distributions, although other distributions may be used. Methods for plotting a probability distribution function for data that forms a normal distribution are known. The probability that a hypothesis is true can be estimated using, e.g., Bayes' theorem, although other methods are known.

The term "confidence" refers to calculated estimate of the reliability of a determination. Confidence can be measured in any suitable way, e.g., using Bayes' theorem and expressed using, e.g., a p-value or a percentage or the like.

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

A method for determining the ploidy of a test genome is provided. In some embodiments, the method may comprises: a) obtaining a plurality of ratios for polymorphisms that are distributed throughout a test genome, wherein each of said ratios is a ratio of the measured copy number of one allele of a polymorphism relative to the measured copy number of said allele in a reference sample that has two copies of said allele; b) plotting a distribution of the ratios to provide a distribution; and c) determining the ploidy of said the genome based on the number of peaks in the distribution. The polymorphisms used in the method may be, e.g., single nucleotide polymorphisms (SNPs), "indels" (i.e., insertions and deletions), inversions, re-arrangements or any other source of sequence variation that can be analyzed on a genome-wide scales.

The relative copy numbers of the alleles that are present at a site of a polymorphism can be measured experimentally using any convenient means. For example, in one embodiment, the amount of a specific allele of a polymorphism in a genome can be determined by DNA sequencing. In this embodiment, the relative amounts of the alleles at a site of a polymorphism may be measured by determining the number of times one allele of the polymorphism is sequenced relative to the number of times the other allele of the polymorphism is sequenced. In other embodiments, the copy numbers of the alleles can be determined by using, e.g., allele-specific PCR (see, e.g., Lin, et al *Multiplex genotype determination at a large number of gene loci*. Proc. Natl. Acad. Sci. 1996 93: 2582-2587), allele-specific hybridization (Matsuzaki, H. et al. *Parallel genotyping of over 10,000 SNPs using a one-primer assay on a high-density oligonucleotide array*. Genome Res. 2004 14: 414-425), primer-extension or ligation based assays, e.g., (Shumaker et al, *Mutation detection by solid phase primer extension*. Hum. Mutat. 1996 7, 346-354), cleavage-based assays or the method of Sampas (US20090035762). Alternative approaches are provided by Mei et al (Genome Res. 2000 10: 1126-37) and Gunderson et al (Nat Genet. 2005 37:549-54).

In certain embodiments, the data may be obtained experimentally by subjecting a test genome to CGH and polymorphism analysis to obtain: i. CGH data indicating which parts of the test genome are putatively diploid and which parts are putatively non-diploid; and ii. polymorphism data comprising ratios indicating the copy number of a plurality of polymorphisms that are present in putatively diploid regions of the test genome.

The assay may provide allele-specific copy number data for a significant number of distinct polymorphisms, e.g., at least 100 polymorphisms (e.g., at least 500, at least 1,000 or at least 5,000 or more polymorphisms) in a genome in order to provide statistically significant results. In particular cases, the polymorphisms may be distributed throughout the genome. For example, the method may utilize data for polymorphisms that are present on every chromosome of a genome. In certain embodiments, data for polymorphic sites that are situated at multiple positions (e.g., 5 to 100 or 10 to 1000 or more positions) on every chromosome may be used.

Figure 2:
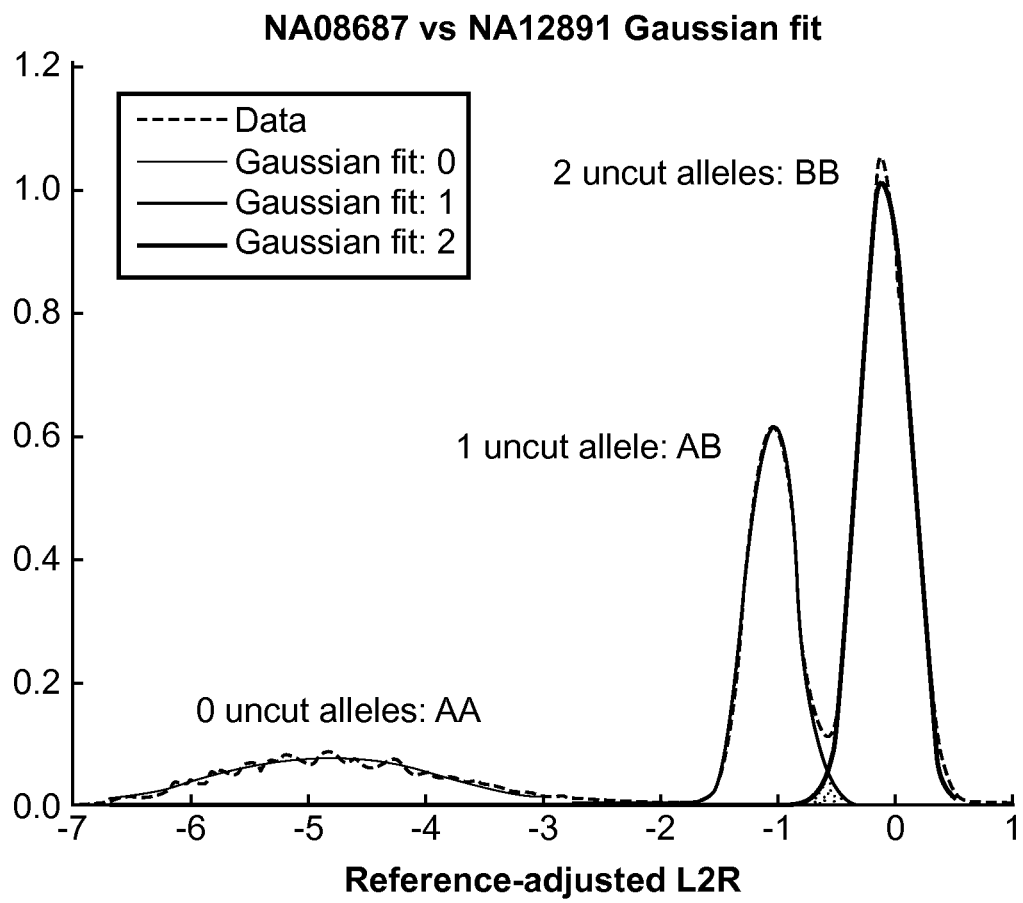
FIG. 2 is a plot of the distribution has three nearly Gaussian peaks that correspond to homozygous alleles (AA and BB) and heterozygous alleles (AB) in a diploid sample.
Figure 3:
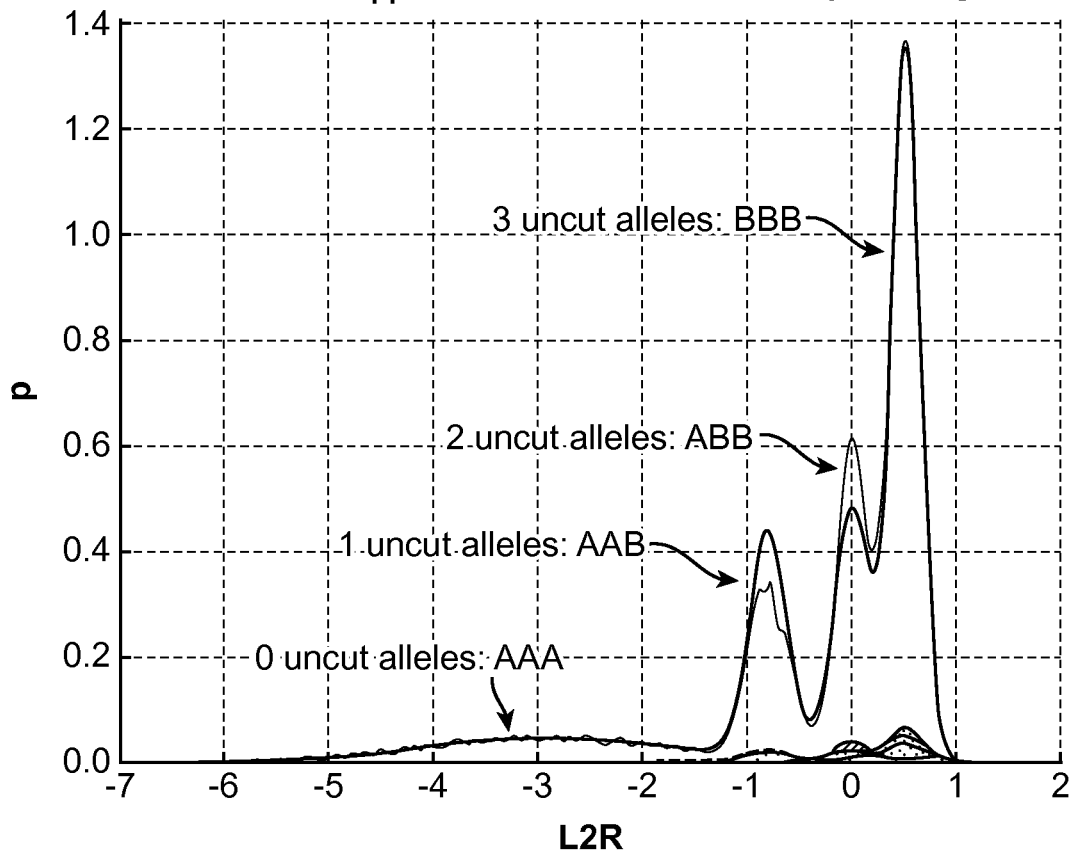
FIG. 3 is a plot of the distribution has four nearly Gaussian peaks that correspond to homozygous alleles (AAA and BBB) and heterozygous alleles (AAB and ABB) in a triploid sample.

Once the ratios have been obtained, the ratios may be expressed as $\log_2$ ratios and in certain embodiments may be adjusted by subtracting 1 from the $\log_2$ ratios of polymorphisms with one reference copy to provide a set of reference adjusted $\log_2$ ratios. The adjusted $\log_2$ ratios are plotted to provide a distribution. In certain embodiments (as illustrated in FIGS. 2 and 3), the horizontal axis of the distribution indicate a range of ratios that are divided into intervals, and the vertical axis represents the number of ratios that are within each of the intervals. The ploidy of the test genome can be determined based on the number of peaks in the distribution. FIGS. 2 and 3, illustrates the difference in the distribution for diploid and triploid samples.

As shown in FIG. 2, for a diploid sample, the plot of the distribution has three nearly Gaussian peaks that correspond to homozygous alleles (AA and BB) and heterozygous alleles (AB) in the test sample. A distribution of $\log_2$ ratios comprising three peaks therefore indicates that the test genome is diploid. As shown in FIG. 3, for a triploid sample, the plot of the distribution has four nearly Gaussian peaks that correspond to homozygous alleles (AAA and BBB) and heterozygous alleles (AAB and ABB) in the test gene. A distribution of $\log_2$ ratios comprising three peaks indicates that the test genome is diploid. A distribution of $\log_2$ ratios comprising four peaks therefore indicates that the test genome is triploid or tetraploid.

In cases where the test sample is tetraploid, i.e., having four copies of the haploid genome, there are three possibilities. In the first instance of "balanced tetraploidy", the sample may have 2 copies of the maternal genome, and 2 copies of the paternal genome. In this case a plot of the distribution of polymorphisms would contain 3 peaks, corresponding to homozygous alleles (AAAA and BBBB) and heterozygous alleles (AABB) in the test sample. In the second instance, the sample may have 1 copy of the maternal genome, and 3 copies of the paternal genome. In the third instance, the sample may have 3 copies of the maternal genome, and 1 copies of the paternal genome. In both the second and third instances of "unbalanced tetraploidy," the plot of the distribution of polymorphisms will have four nearly Gaussian peaks that correspond to homozygous alleles (AAAA and BBBB) and heterozygous alleles (AAAB and ABBB.) Therefore, if the sample has balanced tetraploidy, it may not be distinguished from a diploid sample. However, if the sample has unbalanced tetraploidy, the distribution may be distinguished from a diploid sample by the presence of four peaks, and the distribution may be distinguished from a triploid sample by the analyzing the intervals of the four peaks.

In certain cases, the determining step of the method may comprise determining the ploidy of the test genome based on the number of peaks and one or more intervals (i.e., distances) between the peaks. In diploid samples, and as illustrated in FIG. 2, the intervals between the heterozygous (AB) and the homozygous BB peak is approximately 1.0, using the $\log_2$ scale on the horizontal axis. In the case of a diploid sample (and as illustrated in FIG. 2) the distribution of $\log_2$ ratios comprises three peaks (the AAB, ABB and BBB peaks) of intervals of approximately 1.00 and 0.58 (again on the $\log_2$ scale). In addition, the ploidy of the sample may comprise determining the ploidy of the test genome based on the number of peaks and the areas under the peaks. For a triploid sample, the second and third peaks have areas that are similar.

In some embodiments, the ploidy of the test genome may be determined automatically by analysis of the distribution of the $\log_2$ ratios by a computer. In these embodiments, a distribution of ratios may be analyzed by a computer that is programmed to determine whether a distribution contains three of four peaks, and, optionally, analyze the intervals between the peaks and the areas under the peaks, thereby determining the ploidy of the sample. In some cases, the ploidy of the test genome may be determined by analysis of the distribution of the $\log_2$ ratios by eye, i.e., by looking at the distribution to determine if it has three or four peaks. In some embodiments, therefore, the method may comprise: a) obtaining a plurality of ratios indicating which alleles of a plurality of polymorphisms (e.g., SNPs) are present in putatively diploid regions of a test genome; b) plotting a distribution of the ratios to provide a distribution comprising four peaks; and c) determining that the test sample is tetraploid or triploid because the distribution comprises four peaks; d) calculating a plurality of probability distribution functions that fit the peaks; and e) estimating the allele-specific copy number of a SNP of the test genome using the plurality of probability distribution functions.

The ratios for polymorphisms can be processed using the methods described above, and the ploidy of the test genome can be identified. In certain cases, the method may further comprise adjusting the polymorphism data depending on whether the test genome is tetraploid or diploid. For example, if the test genome is triploid or tetraploid, the method may comprise adjusted CGH data, and reassigning the allele-specific copy number for each polymorphism based on the adjusted data.

In certain embodiments, because the distributions of log ratios are very nearly normal, they can be modeled to a good approximation by Gaussian distributions. The likelihood that each SNP site has a particular allele-specific copy number can be computed by applying Bayes' rule to the reference corrected $\log_2$ ratios, using the fitted Gaussian distributions i.e. the likelihood of a the data being consistent with occurrence of a particular allele specific copy number can be inferred from the fitted probabilities of possible allele specific copy numbers and observed log ratio In certain embodiments, the ratios obtained from counting the number of aligned reads in the test and reference samples sequenced, the ratios can be preprocessed to remove biases that may be resulting from baseline effects between the two samples and the ratios can be further transformed by a Greary Hinkley transformation such that the transformed ratios are then closer to normal distributions In certain cases, the method may further involve calculating a likelihood score indicating the confidence that the allele-specific copy number of the SNP has been correctly assigned, wherein the score is calculated using the plurality of probability distribution functions. In particular embodiments, the method may further include calculating an expectation value for the allele-specific copy number of a SNP. The method may further comprise calculating a likelihood score for the allele-specific copy number of the SNP indicating the confidence that the allele-specific copy number has been correctly assigned, wherein the score are calculated using the plurality of probability distribution functions. Because the log ratio distributions are well described by a Gaussian model, it is possible to compute the Bayesian likelihoods of the different uncut copy number states for each SNP. The genotype can be called at each SNP as the most likely state, with a confidence equal to the likelihood of that state. Typically, over 90% of SNPs are called with a confidence >95%. These results can be visualized for any genomic region as an expectation value of the allele-specific copy number of the uncut allele.

In particular embodiments, the method may involve estimating the allele-specific copy numbers for a plurality of polymorphisms to provide a dataset of allele-specific copy number estimates; and calculating likelihood scores for the allele-specific copy numbers indicating the confidence that the allele-specific copy numbers have been correctly assigned. The likelihood scores are calculated using the plurality of probability distribution functions. The genotype of the sample at these polymorphic sites is then inferred from the allele-specific copy number estimates, total copy number estimates derived from the surrounding CGH probes and the known genotype of the reference sample at the same polymorphic site. In certain cases, the genotype may not be reported for SNP sites whose likelihood scores are below a threshold, e.g., have a confidence value of less than 0.90, less than 0.92, less than 0.95, less than 0.98 or less than 0.99, etc. In other words, the method may further comprise—filtering an allele-specific copy number call from a dataset if its likelihood scores are below a threshold.

In some embodiments, if the genome is triploid, the probability distribution functions may be re-calculated by, e.g., calculating a first probability distribution function for SNP alleles in triploid regions of the test genome that have a copy number of 0 for SNP alleles that have a reference copy number of 1 or 2; calculating a second probability distribution function for SNP alleles in triploid regions of the test genome that have a copy number of 1 for SNP alleles that have a reference copy number of 1 or 2; calculating a third probability distribution function for SNP alleles in triploid regions of the test genome that have a copy number of 2 for SNP alleles that have a reference copy number of 1 or 2; and calculating a fourth probability distribution function for SNP alleles in triploid regions of the test genome that have a copy number of 3 for SNP alleles that have a reference copy number of 1 or 2. This should result in four probability distribution functions, as described above.

Figure 5:
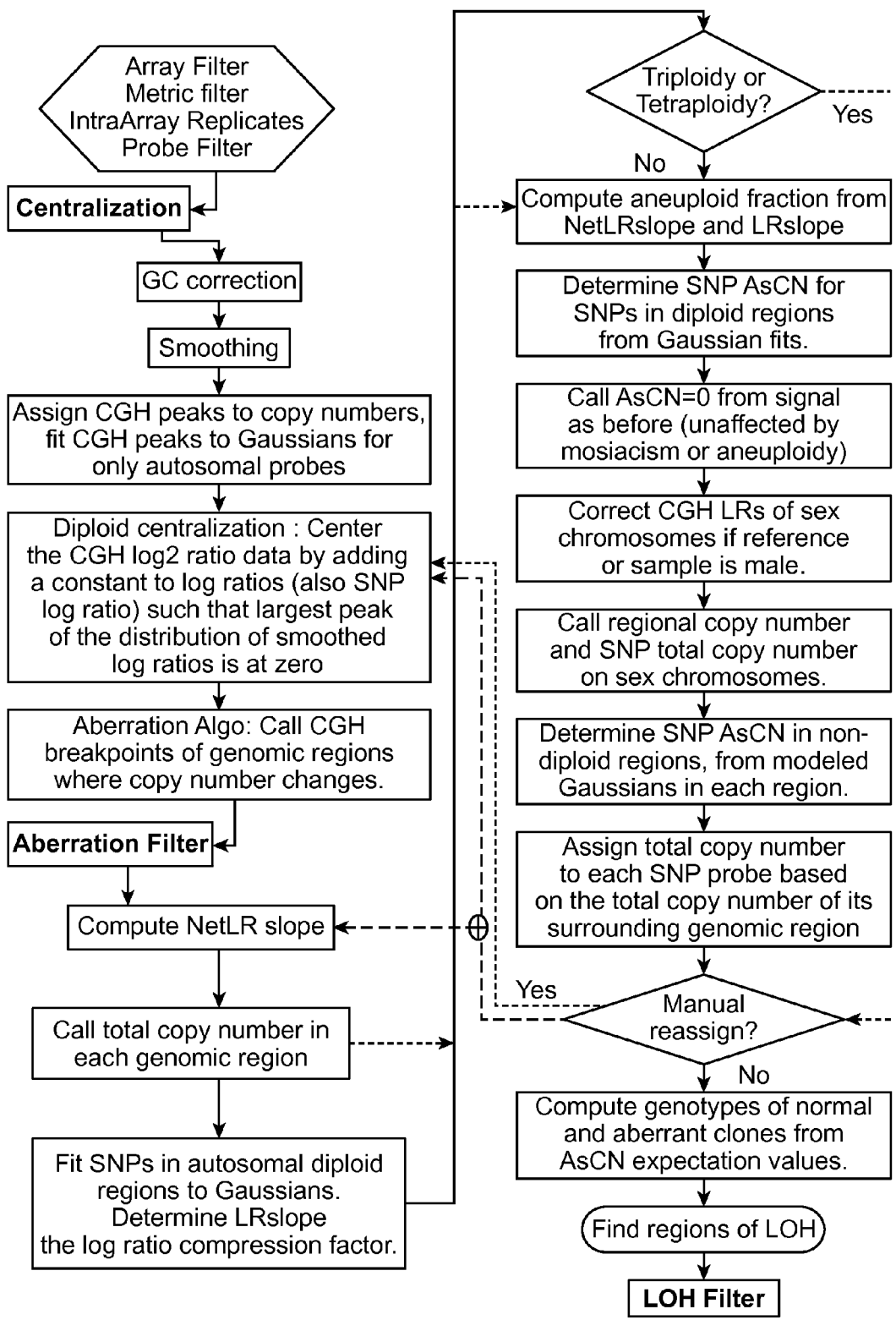
FIG. 5 is a flow-chart illustrating the workflow for one implementation of the method.

In one embodiment, the method may be incorporated into the general workflow described in U.S. patent published US20110301854, by Curry, which method is incorporated by reference for description of that method. FIG. 5 is a flow chart that describes the workflow of an embodiment of the method that is incorporated into the method of Curry described in US20110301854. In one embodiment, diploid samples (including cancer samples with many aberrations) that contain more than a single clone are analyzed as per the steps highlighted according to FIG. 5 starting with the application of different filters on the top left and ending with the LOH (loss of heterozygosity) filter on the bottom right of the diagram. During the analysis workflow, if the SNP data do not fall into a trimodal distribution indicating a diploid sample, a sample is marked as being a constitutional triploid/tetraploid as highlighted in the diamond-shaped decision box, and the workflow splits away from the normal diploid workflow represented by black arrows and continues onward with the computation of the aneuploid fraction. For triploid/tetraploid samples, the workflow skips a number of steps and loops back to the diploid centralization step after correcting for the peak location on the CGH plot to reflect the major ploidy of the sample. The triploid/tetraploid sample executes the aberration-calling algorithm and reassigns copy numbers to aberrant and non-aberrant regions and proceeds to the aneuploid fraction computation that did not run the first time. After completing the remaining workflow steps, the CGH and SNP visualization panes display the correct log ratio values and allele specific copy number values respectively. The manual reassignment step highlighted in the red decision box is available to the user after the computation of SNP allele specific copy numbers and lets the user edit the CGH peak assignments or add/remove CGH peaks. Upon modifying the peak assignments, the workflow loops back to the diploid centralization step if the change occurs in the diploid peak. Alternatively, the loop back repeats the computation of the copy number of each region and the remaining steps as done in the first iteration.

In one embodiment, the workflow for constitutional triploid samples proceeds as follows: (a) Because the entire genome is triploid, only one peak appears in the CGH log ratio distribution. The copy number calling heuristics may initially erroneously assign this peak to diploid. In contrast to aneuploid samples, which have different copy numbers in different genomic regions, an entirely triploid genome cannot be distinguished from a normal diploid genome based on CGH data alone. (b) When the SNP log ratios in putative "diploid" regions are examined, however, four peaks are observed rather than the expected three peaks (see, e.g., FIG. 3). The three peaks of highest log ratios represent the SNPs with 1, 2, or 3 copies of the uncut allele (AsCN). If these peaks appear at the expected intervals (at log ratio intervals of roughly 1 and 0.58), and if the areas of the AsCN=1 and AsCN=2 peaks are comparable (e.g. within a factor of 2.0), then it is highly probable that the SNPs producing these log ratios are present in regions of total copy number three, rather than two as initially assumed. If the peaks appear at the expected intervals of roughly 1.6 and 0.4, then the SNPs producing these log ratios are likely to be present in regions from an unbalanced tetraploidy sample. (c) The copy numbers of all genomic regions are incremented by one, to reflect the reassignment of the diploid genome to triploid. (d) An algorithm to determine SNP genotypes in non-diploid regions was previously reported (see, e.g., US20110301854). This algorithm inputs the Gaussian fits to the AsCN=0, 1, and 2 peaks in diploid regions. This algorithm was modified to provide "corrected" Gaussian fits to AsCN=0, 1, and 2, based on the measured Gaussian fits to AsCN=0,1,2,3 in triploid regions. It should be clear, however, that the genotypes could be determined directly from the Gaussian fits in triploid regions, and that the "corrected" diploid fits are used merely for convenience in implementation. (e) The "corrected" diploid SNP fit to the AsCN=0 genotype is the same as the observed AsCN=0 peak, the "corrected" AsCN=2 peak has mu and sigma equal to those of the observed AsCN=2 peak, but has coefficient equal to that of the observed AsCN=3 peak, and the "corrected" AsCN=1 peak has mu and sigma equal to those of the observed AsCN=1 peak, but has coefficient equal to the sum of those observed for the AsCN=1 and AsCN=2 peaks. Note that this series of steps is essentially the inverse of the algorithm described in US20110301854 that determines genotypes in non-diploid regions. Finally (f) SNP genotypes across the entire genome are computed from the regional copy number and the "corrected diploid" Gaussian fits, as previously disclosed.

In certain cases, allele-specific copy numbers derived from Bayesian likelihoods based on Gaussian probability distributions. That is, the model assumes that the observed log ratio of a SNP probe falls in a Gaussian distribution centered on the log ratio corresponding to the true allele-specific copy numbers of the targeted SNP site. This model has several virtues: first, it arises from a simple physical model of the sources of noise in the assay, second, it is very close to being true (typically less than 1% deviation between modeled and observed log ratios), third, it can easily be parameterized from internal evidence in the data from a single array, without requiring external calibration, and also it is relatively straightforward to compute. The ability to parameterize the model from internal evidence relies statistically on the thousands of SNPs which share the same possible underlying allele-specific copy numbers, in order to be able to stably fit Gaussian distributions. In mosaic samples, each genomic region may have a different mix of fractional allele-specific copy numbers, whose log ratios cannot simultaneously be fit to the same distributions. At the same time, many or most aberrant regions comprise too few SNPs to allow them to be robustly fit independently to Gaussian distributions. The globally similar noise distribution among probes in a single assay estimates probable Gaussian distributions of signals arising from AsCN states in regions that are too sparse to fit independently.

In one embodiment, one or more of the steps of the method may implemented by a computer. A tangible computer-readable medium containing instructions (i.e. "programming") for performing the method described above. The programming can be provided in a physical storage or transmission medium. A computer receiving the instructions can then execute the algorithm and/or process data obtained from the subject method. Examples of storage media that are computer-readable include floppy disks, magnetic tape, DVD, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network. In the context of a computer-implemented method, "obtaining" may be accessing a file that stores data.

Figure 4:
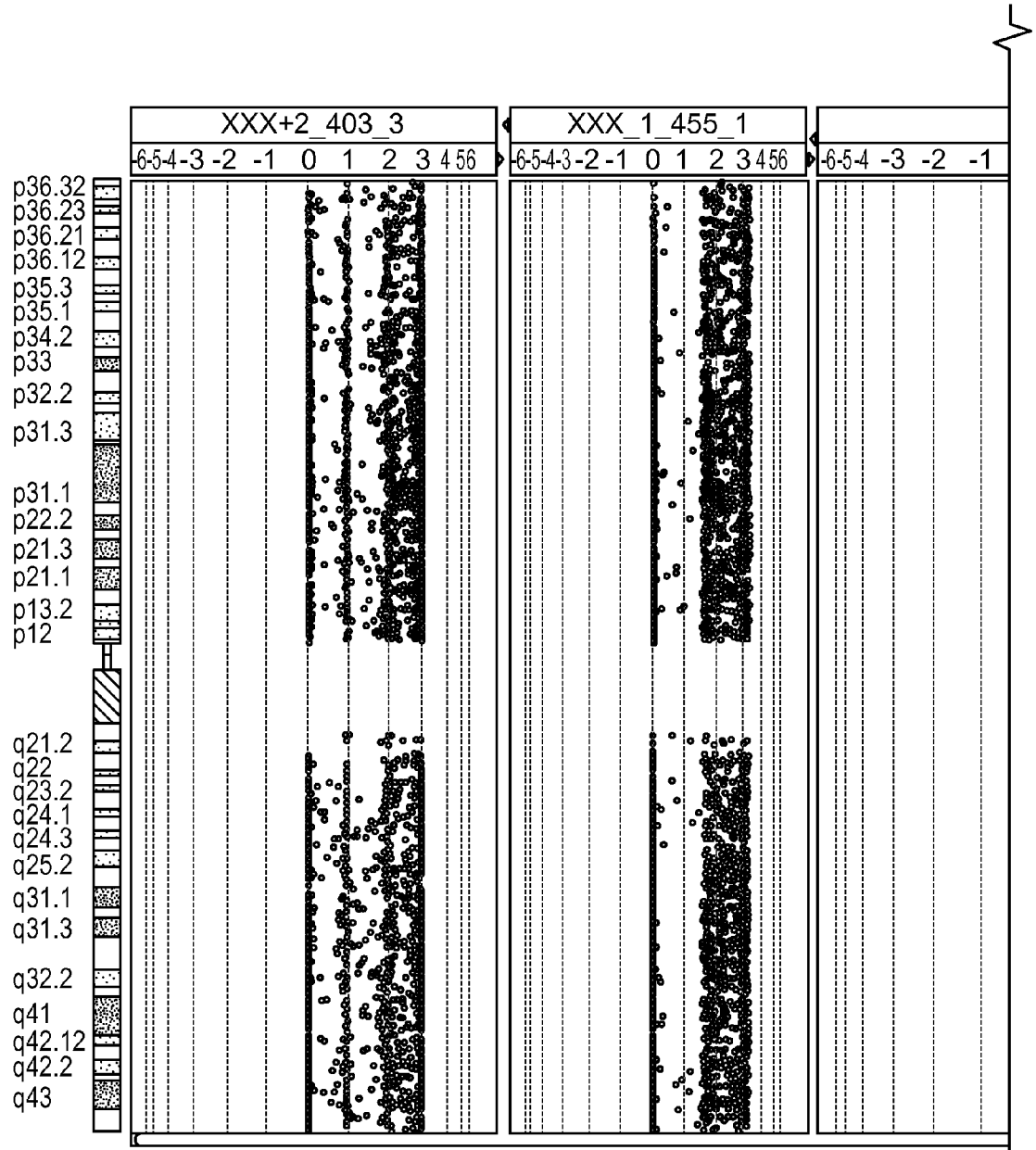
FIG. 4 shows an alignment of a physical map of a chromosome and the allele specific copy numbers of a number of SNPs in a triploid sample.
Figure 4:
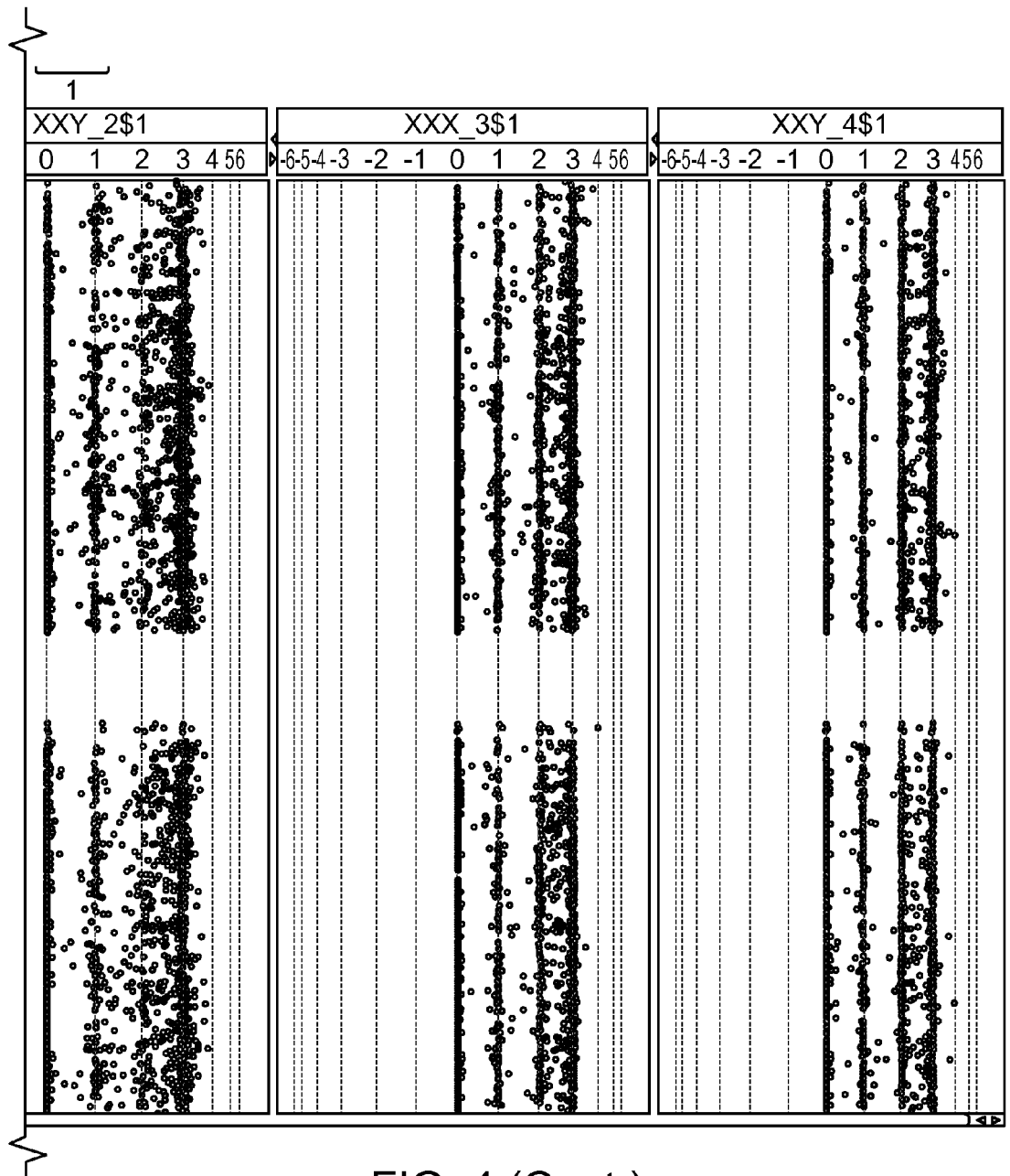

After the data analysis has been performed, the method may further comprise providing a map showing the allele-specific copy number of individual SNPs along a physical region, for example, a map of a single chromosome. In certain cases, this step may involve comparing the test and reference genomes to obtain CGH data and aligning the CGH data with the allele-specific copy number of a plurality of individual SNPs along a physical map to produce an alignment. An example of such a map is illustrated in FIG. 4. This alignment may be used to identify a chromosomal aberration, for example.

The method described above may be incorporated into any analytical method that analyzes the allele specific copy number of SNPs in a genomic sample. In particular cases, the method may be used to determine whether a genomic sample is triploid or tetraploid, and the allele-specific copy number analysis can be adjusted accordingly.

In some embodiments, the ratios are produced by comparing data for a test genome to data for a reference genome. For example, in one embodiment, the method may use a polymorphism-discriminatory probe, where the amount of hybridization of a test genome to the polymorphism-discriminatory probe relative to the amount of hybridization of a reference genome to a polymorphism-discriminatory probe is determined. If there is more of a particular allele in the sample, then there is predictably either more or less hybridization, depending on the details of the assay. In another embodiment, ratios of polymorphism alleles are obtained from the number of sequence reads in a region and likelihood of the different alleles found at a given location given the sequencing and alignment errors.

In certain embodiments and as noted above, the subject method may further include measuring copy numbers of specific nucleotide sequences in combination with identifying which alleles of a polymorphism are present in a sample. In certain cases, the analysis of copy number may also be carried out using the same array, where the hybridization signals of a sample are also used to calculate copy number of sequences in the genomic sample. Additional features may be optionally included on the array to facilitate the analysis. Methods and composition used for assessing copy numbers are described in detail in U.S. Patent Application Pub. Nos. 20070238106 and 20070238108, disclosures of which are incorporated herein by reference.

Further, in some cases, only ratios for polymorphisms that are in regions that are presumed to be diploid may be included in the analysis, where "presumed to be diploid" does not necessarily mean that the regions are indeed diploid. In certain cases, a region is presumed to be diploid because it appears to be diploid in comparative genome hybridization (CGH) analysis. As such, in certain embodiments, the experimental part of the method (which may involve identifying which alleles of a polymorphism are present) may be accompanied by a CGH analysis that indicates the copy number of each of the alleles being measured.

In some embodiments, the ratios were obtained by hybridizing the test and reference genome to an array comprising oligonucleotides that discriminate between different alleles of a SNP. In these embodiments, the amount of each allele of a polymorphism may be measured using the method of Sampas (US20090035762). The principles of the Sampas method are generally described in FIG. 1. U.S. Patent Application Pub. No. 20090035762 is incorporated herein for disclosure of the details of this method, including exemplary probe design protocols, sample preparation protocols, sample labeling protocols, and data analysis protocols. FIG. 1 generally provides a SNP analysis method that comprises: a) contacting a first DNA sample comprising genomic DNA with a first restriction enzyme to provide a digested sample, wherein: i) the DNA sample may comprise a sequence comprising a SNP site; and ii) the first restriction enzyme cleaves the sequence only if a first allele of a SNP is present at the SNP site; b) hybridizing the digested sample to a microarray comprising a probe sequence that is complementary to the sequence comprising the cleavage site; c) comparing the amount of hybridization between the digested sample and the probe sequence to the amount of hybridization between a reference sample and the probe sequence, and d) determining whether the first allele of the SNP is present in the DNA sample, wherein the relative hybridization of the digested sample to the probe as compared to the reference sample indicates whether the first allele of the SNP is present in the DNA sample. As illustrated, cleavage of the sequence at the cleavage site by the first restriction enzyme results in less hybridization of the digested sample relative to a sample in which the sequence is undigested. In these embodiments, the terms "number of uncut copies" or "uncut copy number" both refer to the number of copies of a genomic allele that are not digested by a restriction enzyme. Analogously, the term "cut copy number" refers to the number of alleles that are digested by the restriction enzyme. Uncut copies are detected directly whereas cut copies are inferred at sites for which the total genomic copy number is known.

As noted above, the subject method involves comparing the data derived from a genomic DNA sample to a reference. The reference may also undergo the subject method in the same way as the genomic sample under interest. In other cases, the reference sample is contacted to an array to provide hybridization signals as a control. The reference sequence may be a sequence derived from an identified source or from the same species as the genomic sample under study. The source of the reference may be known to be homozygous or heterozygous for a particular genomic locus of interest. In certain cases, the source may be wild-type for a genomic locus of interest. The source may contain an allelic variant of interest. In certain cases, the reference sequence may be known so that the alleles of the polymorphisms are known.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for determining the ploidy of a test genome, comprising:
    a) obtaining a plurality of ratios for polymorphisms that are distributed throughout a test genome, wherein each of said ratios is a ratio of the measured copy number of one allele of a polymorphism relative to the measured copy number of said allele in a reference sample that has two copies of said allele;
    b) plotting a distribution of the ratios to provide a distribution, wherein one axis of the distribution indicates a range of ratios and another axis of the distribution represents a number of ratios, wherein the distribution comprises a number of peaks; and
    c) determining the ploidy of said test genome based on the number of peaks in said distribution.

2. The method of claim 1, wherein said polymorphisms are single nucleotide polymorphisms (SNPs).

3. The method of claim 1, wherein polymorphisms are on every chromosome in said genome.

4. The method of claim 1, wherein said ratios are produced by comparing data obtained from microarray or NGS data.

5. The method of claim 1, wherein said ratios are $\log_2$ ratios.

6. The method of claim 1, wherein a distribution of $\log_2$ ratios comprising three peaks indicates that said test genome is diploid.

7. The method of claim 1, wherein a distribution of $\log_2$ ratios comprising four peaks indicates that said test genome is triploid.

8. The method of claim 1, wherein said determining comprises determining the ploidy of said test genome based on said number of peaks and the intervals between the peaks.

9. The method of claim 8, wherein a distribution of $\log_2$ ratios comprising three peaks at intervals of approximately 1.00 and 0.58 indicate a triploid sample.

10. The method of claim 1, wherein said determining comprises determining the ploidy of said test genome based on said number of peaks and the areas under the peaks.

11. The method of claim 10, wherein a distribution of $\log_2$ ratios that has four peaks, the second and third peaks of which having areas that are similar, indicates that said test genome is triploid.

12. The method of claim 1, wherein said ratios are obtained by hybridizing said test and reference genome to an array comprising oligonucleotides that discriminate between different alleles of a SNP.

13. The method of claim 1, wherein the ploidy of the test genome is determined automatically by analysis of said distribution by a computer.

14. The method of claim 1, wherein said obtaining is done by subjecting a test genome to CGH and SNP analysis to obtain:
    i. CGH data indicating which parts of said test genome are putatively diploid and which parts are putatively non-diploid; and
    ii. SNP data comprising ratios indicating the allele-specific copy number of a plurality of SNPs that are present in putatively diploid regions of said test genome;
    iii. SNP data comprising ratios for a plurality of SNPs that are present in putatively non-diploid region of said genome.

15. The method of claim 14, wherein said method comprises adjusting said CGH data if said test genome is tetraploid or diploid.

16. The method of claim 1, wherein said method comprises:
    a) obtaining a plurality of ratios indicating which alleles of a plurality of single nucleotide polymorphisms (SNPs) are present in putatively diploid regions of a test genome and a reference genome;
    b) plotting a distribution of the ratios to provide a distribution comprising four peaks; and
    c) determining that said test sample is tetraploid or triploid because said distribution comprises four peaks;
    d) calculating a plurality of probability distribution functions that fit said peaks; and
    e) estimating the allele-specific copy number of a SNP of said test genome using said plurality of probability distribution functions.

17. The method claim 16, comprising:
    calculating a likelihood score for said allele-specific copy number of said SNP indicating the confidence that said allele-specific copy number has been correctly assigned, wherein said score are calculated using said plurality of probability distribution functions.

18. The method of claim 17, further comprising removing allele-specific copy number from a dataset if its likelihood scores are below a threshold.

19. The method of claim 17, wherein said calculating of step d), comprises:
    calculating a first probability distribution function for SNP alleles in triploid regions of said test genome that have a copy number of 0 for SNP alleles that have a reference copy number of 1 or 2;
    calculating a second probability distribution function for SNP alleles in triploid regions of said test genome that have a copy number of 1 for SNP alleles that have a reference copy number of 1 or 2;

calculating a third probability distribution function for SNP alleles in triploid regions of said test genome that have a copy number of 2 for SNP alleles that have a reference copy number of 1 or 2; and calculating a third probability distribution function for SNP alleles in triploid regions of said test genome that have a copy number of 3 for SNP alleles that have a reference copy number of 1 or 2.

20. A tangible computer readable medium comprising instructions for performing the method of claim 1.

* * * * *

UNITED STATES PATENT AND TRADEMARK OFFICE
CERTIFICATE OF CORRECTION

PATENT NO.         : 9,193,992 B2
APPLICATION NO.    : 13/894886
DATED              : November 24, 2015
INVENTOR(S)        : Bo U. Curry et al.

It is certified that error appears in the above-identified patent and that said Letters Patent is hereby corrected as shown below:

On the title page, item (56), in column 2, under "Other Publications", line 12, delete "Biosrtatistics" and insert -- Biostatistics --, therefor.
On the page 2, in column 1, under "Other Publications", line 17, delete "Molercular" and insert -- Molecular --, therefor.
Specification
In column 10, line 50, delete "a the" and insert -- the --, therefor.
In column 10, line 53, delete "ratio" and insert -- ratio. --, therefor.
In column 10, line 58, delete "Greary" and insert -- Geary --, therefor.
In column 10, line 60, delete "distributions" and insert -- distributions. --, therefor.
Claims
In column 16, line 49, in claim 17, after "method" insert -- of --, therefor.

Signed and Sealed this
Fifth Day of July, 2016

Michelle K. Lee
*Director of the United States Patent and Trademark Office*